United States Patent
Iskander et al.

(10) Patent No.: US 8,461,851 B2
(45) Date of Patent: Jun. 11, 2013

(54) SYSTEMS FOR TRANSVERSE ELECTROMAGNETIC MODE IN-SITU SOIL TESTING

(75) Inventors: Magdy F. Iskander, Honolulu, HI (US); Hyoungsun Youn, Honolulu, HI (US); Charles Amazeen, Arlington, VA (US); Brian Burns, Alexandria, VA (US)

(73) Assignee: University of Hawaii, Honolulu, HI (US)

( * ) Notice: Subject to any disclaimer, the term of this patent is extended or adjusted under 35 U.S.C. 154(b) by 259 days.

(21) Appl. No.: 12/757,859

(22) Filed: Apr. 9, 2010

(65) Prior Publication Data

US 2011/0169505 A1 Jul. 14, 2011

Related U.S. Application Data

(60) Provisional application No. 61/268,142, filed on Jun. 8, 2009, provisional application No. 61/186,397, filed on Jun. 12, 2009.

(51) Int. Cl.
*G01R 27/04* (2006.01)

(52) U.S. Cl.
USPC ............... 324/637; 324/642; 324/639

(58) Field of Classification Search
USPC .................................... 324/637–646
See application file for complete search history.

(56) References Cited

U.S. PATENT DOCUMENTS 7,239,150 B2 * 7/2007 Troxler et al. ............... 324/643

OTHER PUBLICATIONS

Hasan, S.M. Shajedul; "Measurement of Dielectric Properties of Materials using Transmission/ Reflection Method with Material Filled Transmission Line". May 19, 2005, IEEE IMTC 2005—Instrumentation and Measurement Technology Conference, pp. 72-77.*

* cited by examiner

*Primary Examiner* — Melissa Koval
*Assistant Examiner* — Feba Pothen
(74) *Attorney, Agent, or Firm* — Leighton K. Chong

(57) ABSTRACT

A slotted TEM transmission line and an in-situ TEM transmission line are utilized to determine both complex permittivity and permeability of soil. The permittivity and permeability information may be used by underground sensing techniques such as GPR and EMI to enhance information from these techniques. The in-situ probe provides that both complex permittivity and permeability can be measured simultaneously over a broad frequency range without disturbing the soil conditions.

7 Claims, 8 Drawing Sheets

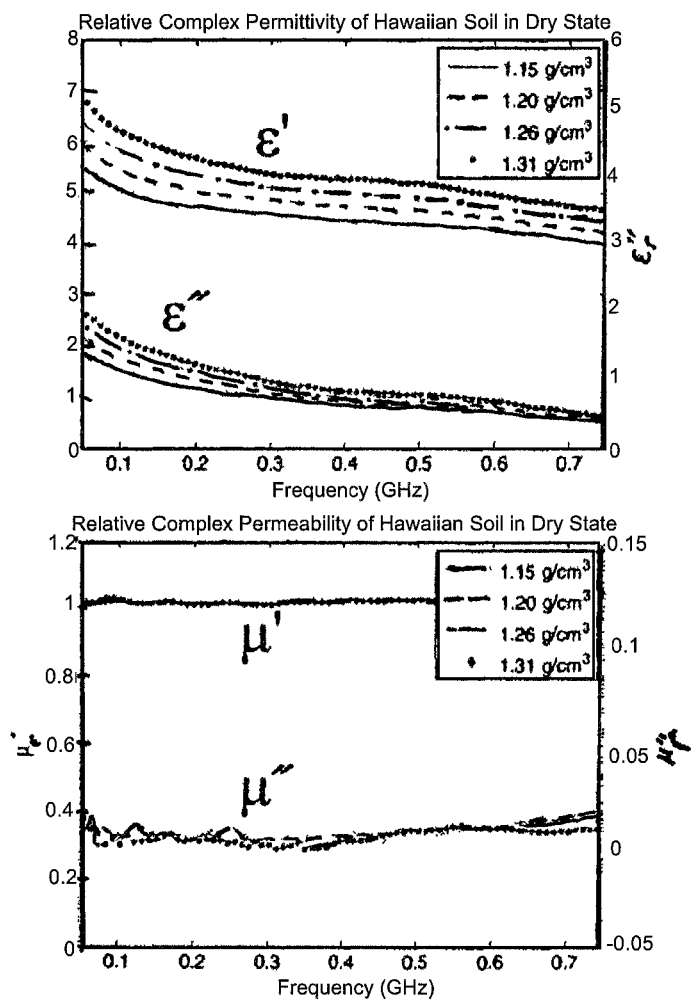
Figure 5 The complex permittivity and permeability of a volcanic Hawaiian soil with different densities.

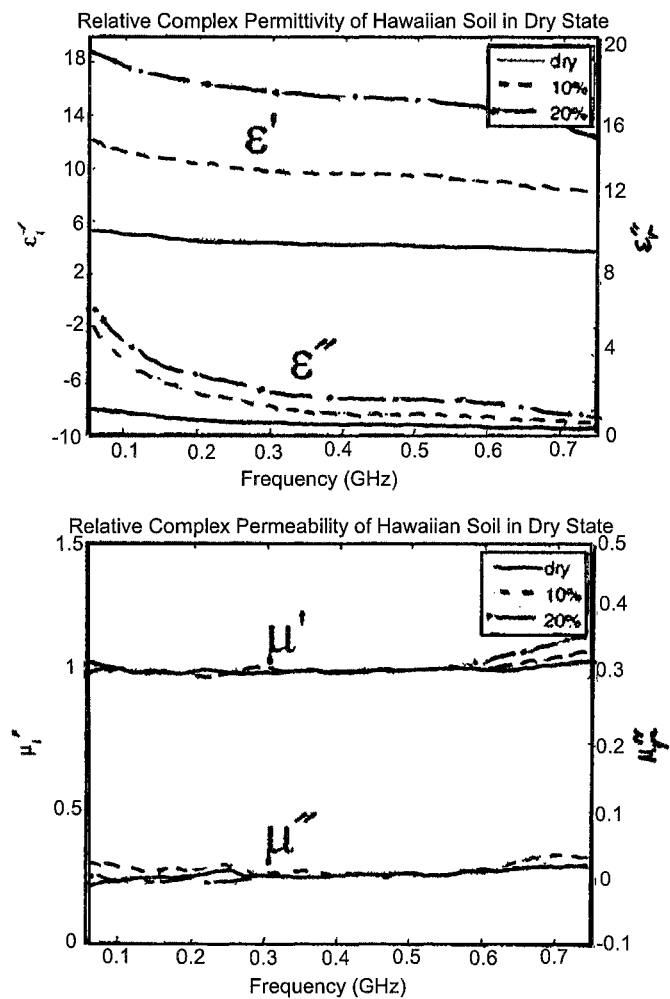
Figure 6 The complex permittivity and permeability of a volcanic Hawaiian soil with different levels of moisture contents.

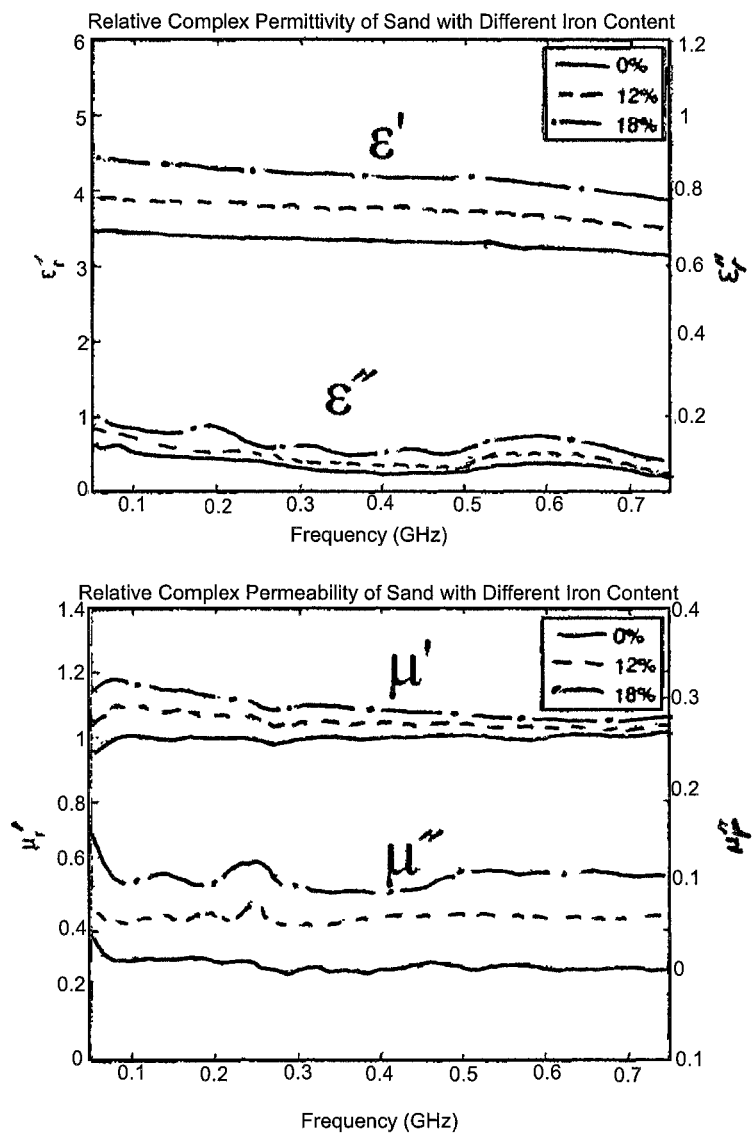
Figure 7 The complex permittivity and permeability of sand and iron grain mixture with different levels of iron contents.

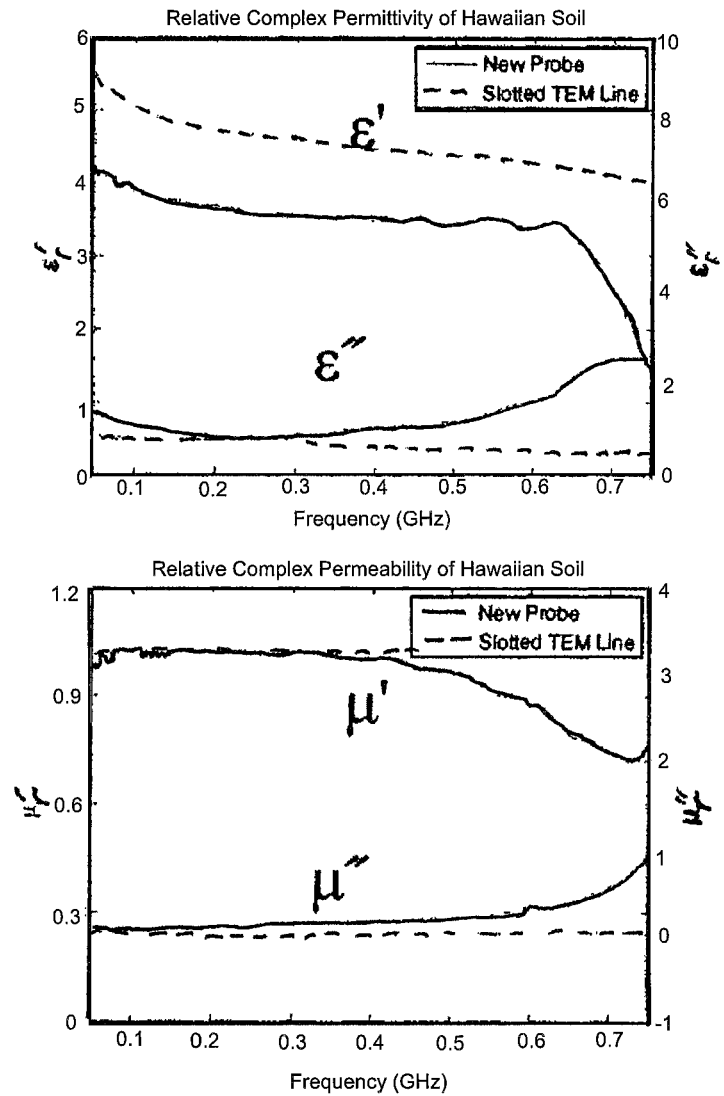
Figure 8  Electromagnetic soil property measured by the slotted TEM transmission and by the three-conductor in-situ probe.

SYSTEMS FOR TRANSVERSE ELECTROMAGNETIC MODE IN-SITU SOIL TESTING

CROSS-REFERENCE TO RELATED APPLICATIONS

This application claims priority to U.S. Provisional Patent Application No. 61/268,142, filed on Jun. 8, 2009, and U.S. Provisional Patent Application No. 61/186,397, filed on Jun. 12, 2009, the disclosures of which are incorporated herein by reference in their entirety.

STATEMENT REGARDING FEDERALLY SPONSORED RESEARCH

This invention was made with the support of the United States Government, Department of Defense, Army Research Development and Engineering Center, contract W909MY-07-C-0025. The United States Government has certain rights in this invention.

FIELD

This disclosure is directed to measurement of electric and magnetic properties of soil.

BACKGROUND

Electromagnetic sensors are commonly used to obtain information about underground environments and objects. Ground Penetrating Radar (GPR), for example, has been utilized as an important tool for investigating many underground environments and objects. Electromagnetic induction (EMI) is also commonly utilized to detect objects that may be located underground. Accurate and meaningful interpretation of data from electromagnetic sensors requires knowledge of the electromagnetic properties of the soil. For example, because GPR signals penetrate through the soil, the electromagnetic properties of the soil are needed to obtain useful information from GPR sensors. The soil properties of many regions are determined for the most part by the water contents and density of soil, which significantly modify permittivity of soil, but not permeability. For this reason, traditional focus has been on measuring the permittivity of soil to predict GPR signal behavior in the soil, while permeability of soil was assumed to be uniform. However, soil in many regions may not have uniform permeability. For example, in iron-rich soil environments behavior of the electromagnetic (EM) wave has been found to also be affected by the iron contents of soil. Also, magnetic soil has been reported to adversely affect the performance of metal detectors. Thus, in such cases, the permeability of soil should also be considered to analyze the performance of EM sensors, such as GPR and EMI sensors. In such iron-rich environments, both permittivity and permeability of soil are essential to analyze GPR data and thus required to be measured simultaneously.

SUMMARY

Embodiments disclosed herein provide soil measurement devices that allow for the determination of soil permittivity and permeability, thereby providing for enhanced utilization of GPR and EMI. GPR and EMI may be used, for example, in locating unexploded ordinance hidden underground. In one aspect, a slotted transverse electromagnetic mode (TEM) transmission line is adapted as a soil sample holder and used to measure impedance of a sample over a desired frequency range. Such a slotted TEM transmission line device requires a certain amount of soil sample to be packed into the sample holder to measure the soil properties. This procedure, in some cases, causes a distortion of the original soil properties, because soil properties are a function of density and moisture. In another aspect, in order to measure the undisturbed soil properties, a three conductor transmission line is provided for in-situ soil measurement.

In one embodiment, the present disclosure provides a soil probe for use in determining permittivity and permeability of a soil sample, comprising: (a) a slotted TEM transmission line, (b) a first port interconnected to a first end of the slotted TEM transmission line; (c) a second port interconnected to a second end of the slotted TEM transmission line; and (d) a soil sample receiver in the slot of the TEM transmission line. The first and second ports of this embodiment are adapted to be connected to a network analyzer that provides electromagnetic signals thereto and receives electromagnetic signals reflected and radiated from the soil and received at said slotted TEM transmission line. A length of the soil sample receiver may be selected to be different than a half-wavelength multiple of signal frequencies received at said slotted TEM transmission line. In an embodiment, the first port and second port comprise coaxial connectors. Each of the coaxial connectors comprises a center conductor that is interconnected to said slotted TEM transmission line and the soil sample receiver is placed to minimize air gaps between the sample and each center conductor. In an embodiment, the slotted TEM transmission line receives electromagnetic signals in the frequency range from about 50 MHz to about 1 GHz through said first and second ports. Impedance of the slotted TEM transmission line may be measured over the frequency range to provide for simultaneous determination of permittivity and permeability of the soil sample.

In another embodiment, the present disclosure provides a soil probe for use in determining permittivity and permeability of a soil sample, comprising: (a) a TEM transmission line comprising a plurality of metal rods interconnected at a first end to a first ground plate, and removably interconnected at a second end to a second ground plate; (b) a first port interconnected to the first ground plate; and (c) a second port interconnected to the second ground plate. The metal rods are configured to be inserted into an in-place soil sample and the first and second ports adapted to be connected to a network analyzer that provides electromagnetic signals thereto and receives electromagnetic signals reflected and radiated from the soil and received at the TEM transmission line. The TEM transmission line may comprise three metal rods. A first metal rod is interconnected with the center conductor of each coaxial connector, and second and third metal rods are each interconnected with an outer conductor of each coaxial connector. The TEM transmission line receives and sends electromagnetic signals in the frequency range from about 50 MHz to about 1 GHz through said first and second ports. Impedance of the TEM transmission line may be measured over the frequency range to provide for simultaneous determination of permittivity and permeability of the soil sample.

In still another embodiment, the present disclosure provides a system for measuring reflection and radiation from a soil sample, the reflection and radiation usable to determine permittivity and permeability of the soil sample, comprising: (a) a soil probe comprising a TEM transmission line and first and second ports; (b) a transmitter that generates electromagnetic energy across a frequency band of interest and forwards the electromagnetic energy to the first and second ports; (c) an impedance measurement circuit that measures an input impedance of the soil probe over the frequency band and generates measured impedance data, the impedance data providing for simultaneous determination of permittivity and permeability of the soil sample. A network analyzer may include the transmitter and impedance measurement circuit.

BRIEF DESCRIPTION OF THE DRAWINGS

FIG. 5 is a graph of the complex permittivity and a graph of the complex permeability of a volcanic soil with different densities;

FIG. 6 is a graph of the complex permittivity and a graph of the complex permeability of a volcanic soil with different moisture contents;

FIG. 7 is a graph of the complex permittivity and a graph of the complex permeability of a sand and iron grain with different levels of iron content; and FIG. 8 is a graph of the complex permittivity and a graph of the complex permeability of a volcanic soil as measured by probes of different embodiments described herein.

DETAILED DESCRIPTION

The present disclosure recognizes that in order to obtain useful information from electromagnetic sensors used in ground penetrating applications, both permittivity and permeability of soil are needed in many instances. Aspects of the present disclosure disclose the measurement of electromagnetic properties of the materials at microwave frequency.

Several microwave methods have been developed and published in material science, and have been applied to estimate the soil properties at frequencies of interest. Generally, soil property measurement methods can be divided into non-resonant and resonant methods. Resonant methods utilize the fact that permittivity and permeability of a dielectric resonator with a certain dimension determines its resonant frequency and quality factor. This method is suitable for accurate measurement of soil properties at a single frequency. On the other hand, non-resonant methods utilize reflection of the EM wave from the soil interface and the transmission through the soil to estimate a general electromagnetic property of the soil over a frequency range. The non-resonant method can be divided into reflection method and reflection/transmission method. The reflection method can only measure one parameter which is permittivity of soil on the assumption of uniform permeability, while the reflection/transmission method can be used in the measurement of both permittivity and permeability. For general GPR environments, the resonance or the reflection method have traditionally been used to measure complex permittivity of soil of interest on the assumption that its permeability is unity. However, for iron-rich soil, the reflection/transmission method is necessary to obtain both complex permittivity and permeability.

For the reflection/transmission method, coaxial transmission lines are widely used as a sample holder to measure reflection (S11) and transmission (S21) of the soil sample due to its broadband frequency coverage. However, the coaxial lines introduce severe measurement uncertainty due to air gaps between the sample and the center conductors. In one embodiment, a slotted TEM transmission line is adapted as a sample holder to reduce this uncertainty because it provides access to both sides of the center conductor and thus can minimize the air gaps between the sample and the center conductor. Such a TEM transmission line method requires a certain amount of soil sample to be packed into the sample holder to measure the soil properties. This procedure inevitably causes an undesirable distortion of the original soil properties, since the soil properties are a function of its density and moisture contents. Therefore, in order to measure the undisturbed soil properties, certain embodiments provide a three conductor transmission line method for in-situ soil measurement.

Figure 1:
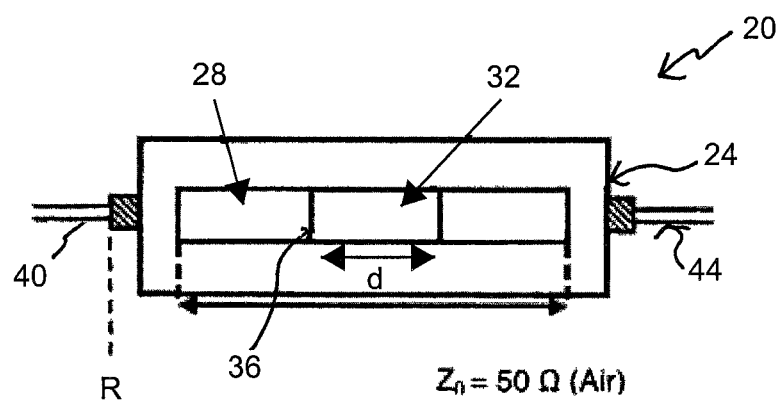
FIG. 1 is an illustration of a soil measurement device according to an exemplary embodiment of the disclosure.

With reference now to FIG. 1, a detailed structure of the novel in-situ soil probe and its calibration method will be discussed for an embodiment. FIG. 1 shows, for an embodiment, a slotted TEM transmission line measurement apparatus 20. In this embodiment, a slotted transmission line 24 has a known characteristic impedance, 50 ohm in this exemplary embodiment, when it is filled with the air. Such a slotted TEM transmission line may be a commercially available transmission line, such as a Hewlett Packard 805e transmission line available from Hewlett Packard, Corp, Palo Alto, Calif. The slotted TEM transmission line 24 includes a slot 28, with and may have a soil sample to be tested inserted into a segment 32 of transmission line through the slot 28. In this embodiment, a plastic sample holder 36 holds the soil sample in segment 32. The slotted TEM transmission line 24 includes a first port 40 and a second port 44 that provide inputs to, for example, a two port network analyzer. The network analyzer in this embodiment collects scattering coefficients $S_{11}$ and $S_{21}$, in the frequency range from 50 MHz to 1.0 GHz.

In one embodiment, the measurement procedure is as follows. First, the slotted transmission line 24 filled with air is connected at port two of a network analyzer through a coaxial cable. Then a standard two port calibration is performed at the calibration plane indicated by R in FIG. 1. In other words, the slotted transmission line 24 is included in the cable section connected to port two and then both port one and two are calibrated at the reference plane (R). The soil sample holder 36 is then filled with the soil sample and the two-port measurements are made. These measurements provide the scattering coefficients ($S_{11}$ and $S_{21}$) of the slotted transmission line 24 with the soil sample. The permittivity and permeability of the soil sample can be calculated by the Nicolson-Ross (N-R) algorithm. The calculated permittivity and permeability may then be used in conjunction with EM data related to an area associated with the soil sample.

For example, assume the sample holder is filled with a soil sample whose permeability is $\mu=\mu_0\mu_R$ and permittivity is $\in=\in_0\in_R$. Then, the characteristic impedance of the sample holder section is modified and a new characteristic impedance is given by:

$$Z=\sqrt{\mu_R/\in_R}Z_0 \quad (1)$$

where $Z_0$ is the characteristic impedance of the TEM slotted transmission line with the air. The intrinsic reflection coefficient of a wave on the interface from the air-filled line is given by $$\Gamma = \frac{Z - Z_0}{Z + Z_0} = \frac{\sqrt{\mu_R/\varepsilon_R} - 1}{\sqrt{\mu_R/\varepsilon_R} + 1} \quad (2)$$

and the transmission coefficient is given by $$T = \exp\left(-j\frac{\omega d\sqrt{\mu_R \varepsilon_R}}{c}\right) \quad (3)$$

where ω is the angular frequency, c is the speed of light in the air and d is the length of the sample holder.

This intrinsic reflection and transmission coefficients can be expressed by the scattering coefficients measured by the network analyzer through the N-R algorithm. Measured scattering coefficients are given by $$S_{11} = \frac{\Gamma(1 - T^2)}{1 - \Gamma^2 T^2} \quad (4)$$

$$S_{21} = \frac{(1 - \Gamma^2)T}{1 - \Gamma^2 T^2} \quad (5)$$

Using N-R algorithm, the intrinsic reflection coefficient is given by $$\Gamma = X \pm \sqrt{X^2 - 1} \quad (6)$$

with $$X = \frac{(S_{11}^2 - S_{21}^2) + 1}{2 S_{11}} \quad (7)$$

and proper sign in equation (6) should be chosen so that $|\Gamma| \leq 1$. The transmission coefficient is given by $$T = \frac{(S_{11} + S_{21}) - \Gamma}{1 - (S_{11} + S_{21})\Gamma} \quad (8)$$

Therefore, the complex permittivity and permeability can be calculated from [8], as $$\mu_R = \sqrt{K_1 K_2} \quad (9)$$

$$\varepsilon_R = \sqrt{\frac{K_1}{K_2}} \text{ with}$$

$$K_1 = \left(\frac{1 + \Gamma}{1 - \Gamma}\right)^2, \quad K_2 = -\left(\frac{c}{\omega d}\ln\left(\frac{1}{T}\right)\right)^2 \quad (10)$$

It should be noted that the N-R algorithm does not work well at resonance frequencies of the sample holder, where the sample holder length is a multiple of a half wavelength when filled with soil. This fact should be taken into consideration when determining the length of the sample holder, and in the embodiment of FIG. 1 the length of sample holder 36 is selected to have a different length than a half-wavelength multiple.

Figure 2:
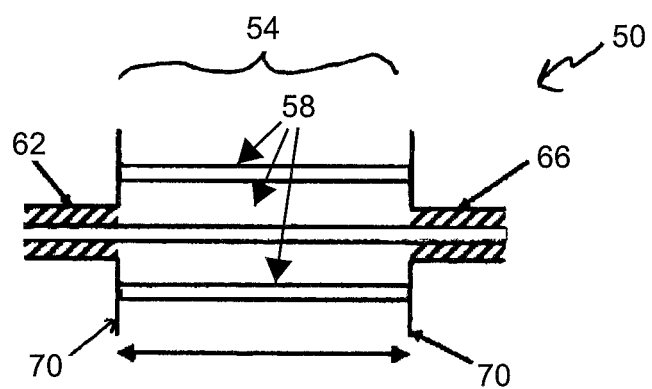
FIG. 2 is an illustration of an in-situ soil measurement device according to another exemplary embodiment of the disclosure.

With reference now to FIG. 2, another embodiment is described in which an in-situ soil test may be obtained. It is recognized that a laboratory measurement is not sufficient to provide the accurate soil properties at a specific time, i.e. the moment of GPR survey. This is because the soil properties vary with the weather conditions and density of the soil. Thus, an in-situ soil probe, which can measure both permittivity and permeability of a soil without disturbing the soil conditions, is useful for better interpretation of GPR data measured in iron-rich soil. Iron-rich soil is present in many environments, such as volcanic soil. In this embodiment, an in-situ soil probe 50 is constructed having a TEM transmission line 54. The TEM transmission line 54 of this embodiment has three metal rods 58, a first port 62, a second port 66, and two ground plates 70. The two ports 62, 66, in this embodiment include coaxial connectors. The center conductors of both coaxial connectors for ports 62, 66 are linked by the center metal rod 58. In one embodiment, each metal rod has a ⅛ inch diameter. Ground plates 70 in this embodiment are connected to the outer conductor of the coaxial connectors for ports 62, 66. The ground plates 70 at both sides are connected by the other two metal rods 58. In the embodiment of FIG. 2, the ground plate 70 associated with the second port 66 is detachable from the metal rods 58. This enables the soil probe to be inserted into the soil from the side without disturbing the soil.

Figure 3:
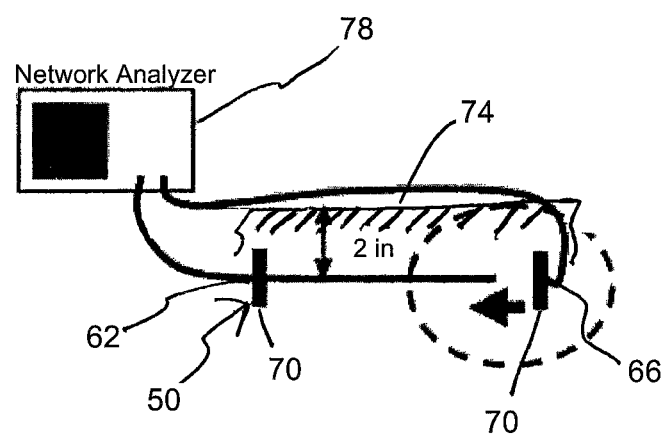
FIG. 3 is an illustration of a soil measurement system according to an exemplary embodiment of the disclosure.
Figure 4:
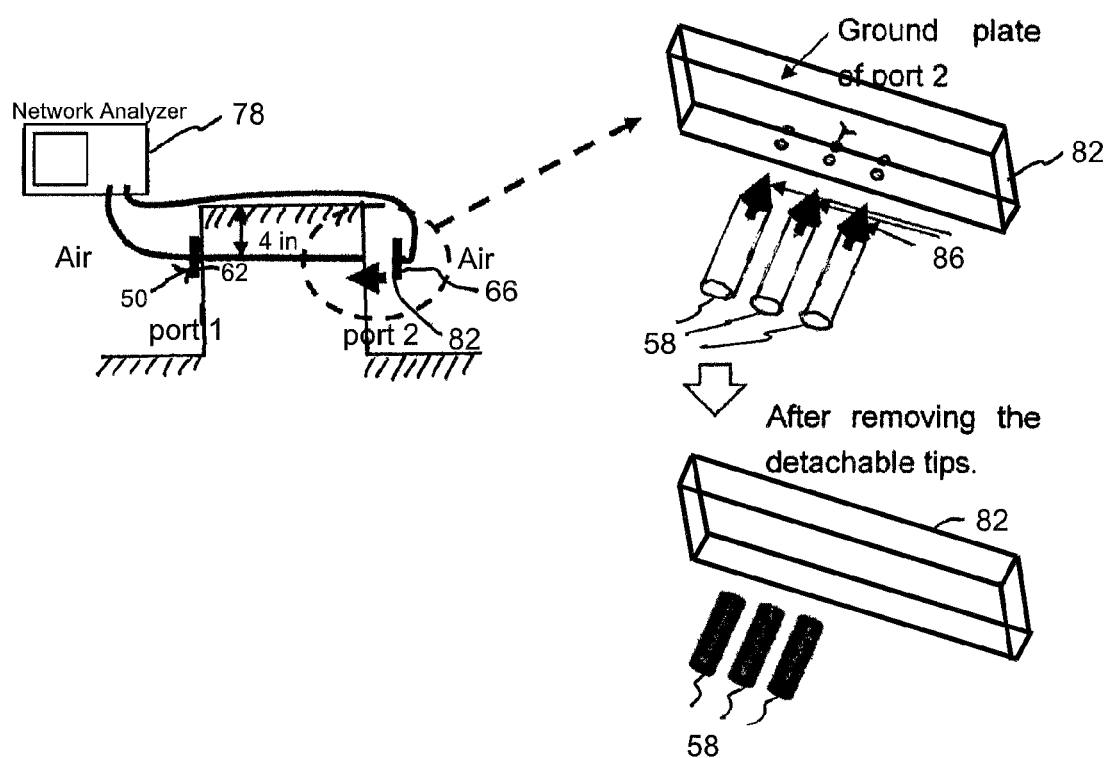
FIG. 4 is an illustration of a soil measurement system according to another exemplary embodiment of the disclosure.

FIG. 3 illustrates an in-situ probe 50 inserted into a soil sample below the surface 74 of the soil. In this embodiment, the probe 50 is inserted at least two inches below the surface 74 of the soil in order to provide suitably accurate readings. It is to be understood that different configurations may require different soil depths. In the embodiment of FIG. 3, a two port network analyzer 78 is connected to each port 62, 66 of the in-situ probe 50 and $S_{11}$ and $S_{21}$ are collected at the network analyzer 78. FIG. 4 illustrates another embodiment with the in-situ probe 50, a ground plate 82 associated with the second port 66 illustrated in an exploded view and having detachable tips 86 that connect metal rods 58.

The in-situ soil probe 50 has a characteristic impedance of the TEM transmission line as modified by equation (1) when it is filled with the soil. Unlike the slotted TEM transmission line, the characteristic impedance of the three-conductor TEM transmission line in the air is not equal to the impedance of the ports (i.e. 50 ohm). Thus, in an embodiment the N-R algorithm is modified and a probe calibration method is provided to calculate the electromagnetic properties of the soil. Calibration and measurement procedures for the in-situ soil probe 50 are as follows for this embodiment. First, the two-port network analyzer 78 is calibrated at the terminal of the coaxial cable. Next the scattering coefficients of the three-conductor transmission line 50 in the air are measured for the probe calibration, from which the characteristic impedance of this transmission line in the air is obtained by $$Z_{TL}^{Air} = Z_0 \frac{1 + \Gamma}{1 - \Gamma} \quad (11)$$

where $Z_0$ is the characteristic impedance of the coaxial cable and $\Gamma$ is the intrinsic reflection coefficient on the interface from the air-filled three-conductor transmission line 50, which can be calculated by equation (6). Then, the in-situ probe is inserted into the soil and collects the scattering coefficients ($S_{11}$ and $S_{21}$). From these measured scattering parameters and the impedance of the transmission line in the air, the complex permittivity and permeability of the soil can be calculated by modified N-R algorithm and it is given by $$\mu_R = \sqrt{J_1 J_2} \qquad (12)$$

$$\varepsilon_R = \sqrt{\frac{J_1}{J_2}} \text{ with}$$

$$J_1 = \left(\frac{Z_0}{Z_{TL}^{Air}} \cdot \frac{1+\Gamma}{1-\Gamma}\right)^2, \quad J_2 = -\left(\frac{c}{\omega d} \ln\left(\frac{1}{T}\right)\right)^2 \qquad (13)$$

where d is the length of the three-conductor TEM transmission line 50.

In one example, the apparatus of FIGS. 2 and 3 were used along with the described measurement methods in experimental studies conducted for iron-rich volcanic Hawaiian soil. Effects of water contents, density and iron contents of the soil on the electromagnetic soil properties were investigated by the laboratory method using the slotted TEM transmission line of FIG. 1. The volcanic soil samples were collected at a typical red soil area in Oahu, Hi. Laboratory soil measurements were conducted for different levels of water contents of soil samples and different densities of soil samples. FIGS. 5 and 6 show the real and imaginary parts of the permittivity and permeability of the volcanic Hawaiian soil with different level of the water contents and different densities. It is well known that the complex permittivity of a soil is proportional to the water contents and density of the soil, which are in agreement with the results as illustrated in FIGS. 5 and 6. On the other hand, the permeability of soil was not influenced by the water contents of soil. The real part of permeability of the volcanic Hawaiian soil indicated approximately from 1.03 to 1.05 over the frequency range, while the imaginary part indicated from 0.004 to 0.012 regardless of density and water contents, which were slightly higher value compared to those of dry sand without iron contents shown in FIG. 7.

With reference to FIG. 7, effects of iron contents on the soil properties are illustrated for three soil samples prepared by mixing the iron grains with sand in different volume fractions. It is believed that the permeability of soil is more sensitive to larger sizes of the iron grain. Thus, the iron grain size in the samples used to generate FIG. 7 were selected to observe variations of the complex permeability, with a size range of 300-600 μm. FIG. 7 plots the complex permittivity and permeability for each sample with different levels of the iron contents. FIG. 7 confirms that both complex permittivity and permeability increase with iron content.

The in-situ soil probe described above was tested in the laboratory with soil samples to evaluate its performance by comparing its result with that of the slotted TEM transmission line of FIG. 1. The results from these measurements are shown in FIG. 8. The real part of permittivity measured by the in-situ probe abruptly decreases with frequency increment from around 650 MHz. This is because frequency is approaching to the resonance frequency of the in-situ probe in the material. As discussed above, the N-R algorithm does not work well near the resonance frequency of the probe in the material. In cases where a GPR or EMI are to be operated near these frequencies, the length of the metal rods in the in-situ probe may be reduced or increased to avoid this result. It is also observed that difference in measurement results of two methods increases with frequency increment. This can be explained by non uniform characteristic impedance of the tested in-situ probe along the transmission line. Since the probe used in generating these data was manufactured manually by relatively inaccurate machines, spacing between three conductors was not perfectly uniform and their alignments were not perfect. This structural variation resulted in non-uniform impedance along the transmission line, which created increased reflection and radiation over the transmission line. These actions are amplified as the frequency increases and causes the error in measurement results.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A soil probe for use in determining permittivity and permeability of a soil sample, comprising:
    a slotted transverse electromagnetic mode (TEM) transmission line having opposite first and second ends and a pair of slot walls extending longitudinally in parallel between said first and second ends and spaced apart by a slot in between the slot walls;
    a first port interconnected to the first end of said slotted TEM transmission line;
    a second port interconnected to the second end of said slotted TEM transmission line; and
    a soil sample receiver of a selected length and configured to be fitted in an intermediate segment of the slot of said slotted TEM transmission line, said soil sample receiver being adapted to receive a soil sample packed therein, said first and second ports being adapted to be connected to a network analyzer that provides electromagnetic signals thereto and receives electromagnetic signals reflected and radiated from the soil held in the soil sample receiver fitted in the intermediate segment of the slot of said slotted TEM transmission line.

2. The soil probe of claim 1, wherein the length of said soil sample receiver is selected to be different than a half-wavelength multiple of signal frequencies received at said slotted TEM transmission line.

3. The soil probe of claim 1, wherein said first port and said second port comprise coaxial connectors.

4. The soil probe of claim 3, wherein each of said coaxial connectors comprises a center conductor that is interconnected to the slot walls of said slotted TEM transmission line and said soil sample receiver is fitted in the intermediate segment of the slot formed between the slot walls in order to minimize air gaps between the sample and each center conductor.

5. The soil probe of claim 1, wherein said slotted TEM transmission line receives electromagnetic signals in the frequency range from about 50 MHz to about 1 GHz through said first and second ports.

6. The soil probe of claim 5, wherein impedance of said slotted TEM transmission line may be measured over said frequency range to provide for simultaneous determination of permittivity and permeability of the soil sample.

7. A system for measuring reflection and radiation from a soil sample, the reflection and radiation usable to determine permittivity and permeability of the soil sample, comprising:
    a soil probe comprising a transverse electromagnetic mode (TEM) transmission line and first and second ports;
    a transmitter that generates electromagnetic energy across a frequency band of interest and forwards the electromagnetic energy to the first and second ports;
    an impedance measurement circuit that measures an input impedance of the soil probe over the frequency band and generates measured impedance data, the impedance data providing for simultaneous determination of permittivity and permeability of the soil sample, wherein said soil probe comprises a slotted TEM transmission line having opposite first and second ends and a pair of slot walls extending longitudinally in parallel between the first and second ends and spaced apart by a slot in between the slot walls, and a soil sample receiver of a selected length that is configured to be fitted into an intermediate segment of the slot of said slotted TEM transmission line and adapted to receive a soil sample packed therein.

* * * * *